United States Patent
Sharma et al.

(10) Patent No.: US 11,873,289 B2
(45) Date of Patent: Jan. 16, 2024

(54) PYRAZOLE COMPOUNDS AND PREPARATION THEREOF

(71) Applicant: MYOKARDIA, INC., Brisbane, CA (US)

(72) Inventors: Sunil Sharma, Gurgaon (IN); Dinesh Jangid, Gurgaon (IN); Priyanka Dhaka, Gurgaon (IN); Siddharth Madhwal, Gurgaon (IN); Bharat Kumar, Gurgaon (IN); Kapil Kumar, Gurgaon (IN); Rajdeep Anand, Gurgaon (IN); Anurag Jain, Gurgaon (IN)

(73) Assignee: MyoKardia, Inc., Brisbane, CA (US)

( * ) Notice: Subject to any disclaimer, the term of this patent is extended or adjusted under 35 U.S.C. 154(b) by 0 days.

(21) Appl. No.: 16/966,502

(22) PCT Filed: Feb. 1, 2019

(86) PCT No.: PCT/IN2019/050076
§ 371 (c)(1),
(2) Date: Jul. 31, 2020

(87) PCT Pub. No.: WO2019/150392
PCT Pub. Date: Aug. 8, 2019

(65) Prior Publication Data
US 2021/0053940 A1 Feb. 25, 2021

(30) Foreign Application Priority Data

| Feb. 1, 2018 | (IN) | 201811003855 |
| Feb. 1, 2018 | (IN) | 201811003859 |
| May 30, 2018 | (IN) | 201711042921 |

(51) Int. Cl.
| C07D 401/12 | (2006.01) |
| C07D 231/12 | (2006.01) |
| C07D 231/18 | (2006.01) |
| B01J 23/72 | (2006.01) |
| B01J 27/122 | (2006.01) |

(52) U.S. Cl.
CPC ............ *C07D 401/12* (2013.01); *B01J 23/72* (2013.01); *B01J 27/122* (2013.01); *C07D 231/12* (2013.01); *C07D 231/18* (2013.01)

(58) Field of Classification Search
None
See application file for complete search history.

(56) References Cited

U.S. PATENT DOCUMENTS

| 2010/0113377 A1 | 5/2010 | Simpson |
| 2016/0244412 A1 | 8/2016 | Dakshinamoorthy et al. |
| 2021/0053940 A1 | 2/2021 | Sharma et al. |

FOREIGN PATENT DOCUMENTS

| EP | 3015458 A1 | 5/2016 |
| EP | 2890682 B1 | 6/2016 |
| JP | 2007284386 A | 11/2007 |
| WO | 2012166415 A1 | 12/2012 |
| WO | 2014033164 A1 | 3/2014 |
| WO | 2014/089913 A1 | 6/2014 |
| WO | 2016118774 A1 | 7/2016 |
| WO | 2018132372 A1 | 7/2018 |
| WO | 2018191283 A1 | 10/2018 |

OTHER PUBLICATIONS

Database Registry Chemical Abstracts Service, Columbus, Ohio, Accession No. RN 1211751-27-7, Entered STN: Mar. 19, 2010.*
Database Registry Chemical Abstracts Service, Columbus, Ohio, Accession No. RN 1970976-14-7, Entered STN: Aug. 10, 2016.*
Database Registry Chemical Abstracts Service, Columbus, Ohio, Accession No. RN 1152556-14-3, Entered STN: Jun. 5, 2009.*
Database Registry Chemical Abstracts Service, Columbus, Ohio, Accession No. RN 1465992-88-4, Entered STN: Oct. 30, 2013.*
Database Registry Chemical Abstracts Service, Columbus, Ohio, Accession No. RN 2055222-83-7, Entered STN: Dec. 30, 2016].*
Database Registry Chemical Abstracts Service, Columbus, Ohio, Accession No. RN 1856047-69-2, Entered STN: Jan. 31, 2016.*
Database Registry; Registry No. 1152556-14-3, entered STN Jun. 5, 2009.
CAS RN 1465992-88-4 (Entered STN Oct. 30, 2013).
12 registry compounds cited by JP (2020-541983) Office Action dated Jan. 24, 2023: "RN 2104044-77-9 entered Jul. 27, 2017", "RN 1497942-42-3 entered Dec. 18, 2013"; "RN 1493355-09-1 entered Dec. 12, 2013"; "RN 1483601-89-3 entered Nov. 29, 2013"; "RN 1481670-85-2 entered Nov. 26, 2013"; "RN 147559-89-1 entered Nov. 24, 2013"; "RN 1468599-50-9 entered Nov. 3, 2013"; "RN 1465992-88-4 entered Oct. 30, 2013"; "RN 1465207-27-5 entered Oct. 30, 2013"; "RN 1361004-09-2 entered Mar. 15, 2012"; "RN 134840-74-3 entered Nov. 10, 2011"; RN 1342785-14-1 entered.

(Continued)

*Primary Examiner* — Samantha L Shterengarts
(74) *Attorney, Agent, or Firm* — Honigman LLP; Andrew S. Chipouras; Jonathan P. O'Brien

(57) ABSTRACT

The present invention provides processes for preparation of substituted pyrazole compounds of formula II, that can be used as intermediates for preparation of substituted piperidine urea compounds useful for the treatment of dilated cardiomyopathy (DCM). $R^2$ is independently selected from F, C1-C4 alkyl, C1-C4 haloalkyl, $R^3$ is independently selected from H, F, C1-C4 alkyl, C1-C4 haloalkyl, $R^4$ is C1-C4 alkyl, $R^6$ is H or a protecting group and $R^7$ is selected from H, CI or trialkylsilyl.

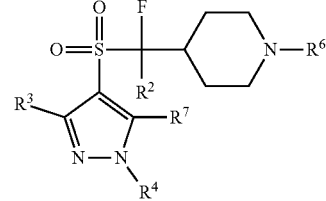

Formula II

32 Claims, No Drawings

(56) References Cited

OTHER PUBLICATIONS

CAS Registry No. 1342785-14-1, Nov. 8, 2011.
PubChem CID 122170329 Oct. 5, 2016.
PubChem CID 46738011 Jul. 26, 2010.
Mini-Reviews in Organic Chemistry, 2008, 5, 331-335.
L. Yet, in Comprehensive Heterocyclic Chemistry III. 2008. "Five-membered Rings with Two Heteroatoms, each with their Fused Carbocyclic Derivatives".

* cited by examiner

PYRAZOLE COMPOUNDS AND PREPARATION THEREOF

CROSS-REFERENCE TO RELATED APPLICATIONS

This application is a 35 U.S.C. § 371 United States National Phase Application of, and claims priority to, PCT Application No. PCT/IN2019/050076, filed Feb. 1, 2019, which claims the benefit of Indian Application Serial No. 201811003855, filed Feb. 1, 2018, Indian Application Serial No. 201811003859, filed Feb. 1, 2018, and Indian Application Serial No. 201711042921, filed May 30, 2018. The entire contents of the aforesaid applications are incorporated by reference herein in its entirety.

FIELD OF THE INVENTION

The present invention provides processes for preparation of substituted pyrazole compounds of formula II, that can be used as intermediates for preparation of substituted piperidine urea compounds useful for the treatment of dilated cardiomyopathy (DCM).

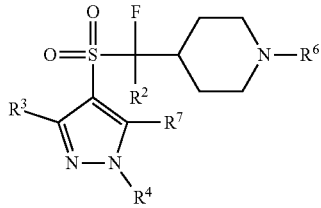

Formula II $R^2$ is independently selected from F, $C_1$-$C_4$ alkyl, $C_1$-$C_4$ haloalkyl; and $R^3$ is independently selected from H, F, $C_1$-$C_4$ alkyl, $C_1$-$C_4$ haloalkyl, $R^4$ is $C_1$-$C_4$ alkyl, $R^6$ is H or a protecting group or salt thereof and $R^7$ is selected from H, Cl or trialkylsilyl.

BACKGROUND OF THE INVENTION

4-Methylsulphonyl substituted piperidine urea compounds of formula I are being developed for the treatment of dilated cardiomyopathy (DCM), a disease that leads to heart failure and severe complications such as stroke, arrhythmias, and sudden cardiac death.

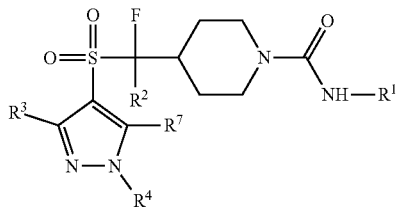

Formula I wherein $R^1$ is a 5 to 6-membered heteroaryl ring having at least one nitrogen atom and is optionally substituted with one or more selected from halo, cyano, hydroxyl, $C_1$-$C_4$ alkyl, $C_1$-$C_4$ haloalkyl, and $C_1$-$C_4$ alkoxy.

WO2016/118774 discloses preparation of 4-methylsulphonyl substituted piperidine urea compounds using reagents like N-Fluorodibenzenesulfonimide, (NFSI), diethylaminosulfur trifluoride, lithiated compounds that are strong, expensive reagents and are not viable for commercial scale up of 4-methylsulphonyl substituted piperidine urea compounds.

There is a need in the art to replace these reagents for preparation of 4-methylsulphonyl substituted piperidine urea compounds of formula I. The present invention provides processes for preparation of substituted pyrazole compounds of formula II that can be used as intermediates for preparation of compound of formula I.

OBJECT OF THE INVENTION

The present invention provides processes for preparation of substituted pyrazole compounds of formula II that can be used as intermediates for the preparation of substituted piperidine urea compounds useful for treatment of dilated cardiomyopathy (DCM).

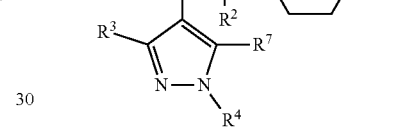

Formula II $R^2$ is independently selected from F, $C_1$-$C_4$ alkyl, $C_1$-$C_4$ haloalkyl; and $R^3$ is independently selected from H, F, $C_1$-$C_4$ alkyl, $C_1$-$C_4$ haloalkyl, $R^4$ is $C_1$-$C_4$ alkyl, $R^6$ is H or a protecting group or salt thereof and $R^7$ is selected from H, Cl or trialkylsilyl.

SUMMARY OF THE INVENTION

In an aspect, the present invention provides a process for preparation of a compound of formula II,

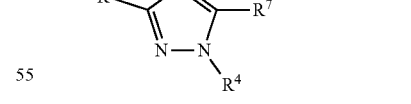

Formula II $R^2$ is independently selected from F, $C_1$-$C_4$ alkyl, $C_1$-$C_4$ haloalkyl, $R^3$ is independently selected from H, F, $C_1$-$C_4$ alkyl, $C_1$-$C_4$ haloalkyl, $R^4$ is $C_1$-$C_4$ alkyl, $R^6$ is H or a protecting group or salt thereof and $R^7$ is a group selected from H, Cl or trialkylsilyl;

comprising the steps of:

a) reacting a compound of formula VII, with elemental sulfur in presence of a base, a catalyst and a reducing agent to give a compound of formula VI;

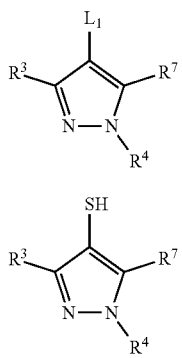

Formula VII

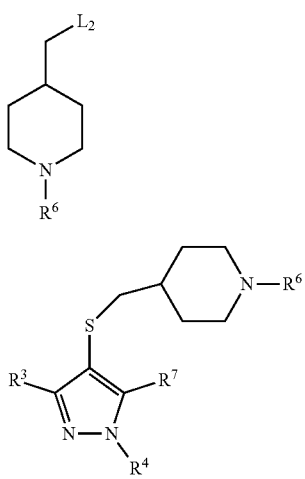

Formula VI wherein R³' R⁴ and R⁷ are as defined above, L₁ is a leaving group b) reacting the compound of formula VI with a compound of formula VIII to give a compound of formula V;

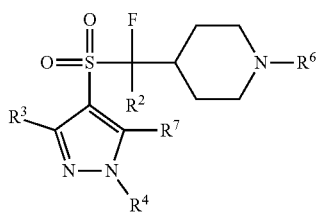

Formula VIII

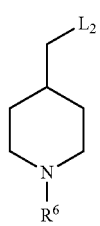

Formula V wherein L₂ is a leaving group; R⁶ is as defined above;

c) converting the compound of formula V to the compound of formula II.

In another aspect, the present invention provides a process for preparation of a compound of formula II, Formula II

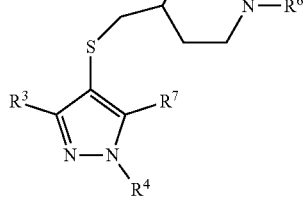

$R^2$ is independently selected from F, $C_1$-$C_4$ alkyl, $C_1$-$C_4$ haloalkyl; and $R^3$ is independently selected from H, F, $C_1$-$C_4$ alkyl, $C_1$-$C_4$ haloalkyl, $R^4$ is $C_1$-$C_4$ alkyl, $R^6$ is H or a protecting group or salt thereof and $R^7$ is selected from H, Cl or trialkylsilyl;

comprising the steps of:

a) reacting a compound of formula VII with an elemental sulfur in presence of base and a catalyst to give a compound of formula VIB, Formula VII

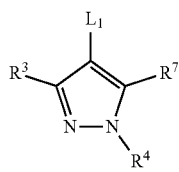

Formula VIB

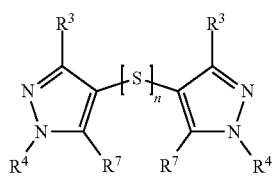

wherein R³ and R⁴ are as defined above, n is 2-8; L₁ is selected from a leaving group;

b) reacting the compound of formula VIB with a compound of formula VIII, to give a compound of formula V Formula VIII

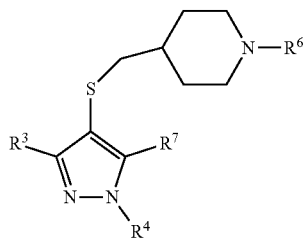

Formula V wherein L₂ is a leaving group;

c) converting the compound of formula V to the compound of formula II.

In another aspect, the present invention provides a process for preparation of a compound of formula II Formula II

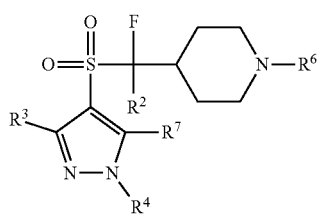

wherein R², R³, R⁴, R⁶ and R⁷ are as defined above;

comprising the steps of:

a) fluorinating a compound of formula V to give a compound of formula IV;

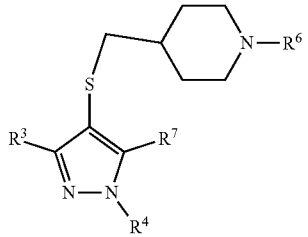

Formula V

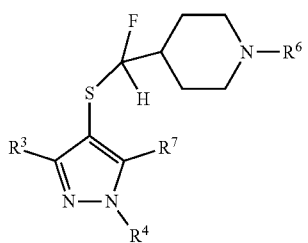

Formula IV b) oxidizing the compound of formula IV to give a compound of formula III

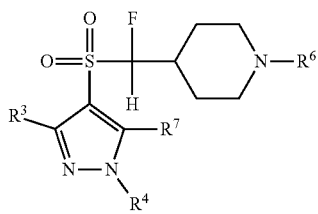

Formula III c) converting the compound of formula III to the compound of formula II.

In another aspect, the present invention provides a process for preparation of a compound of formula II, wherein the steps of fluorination and oxidization are carried out without isolating the compound of formula IV.

In another aspect, the present invention provides a process for preparation of a compound of formula IV,

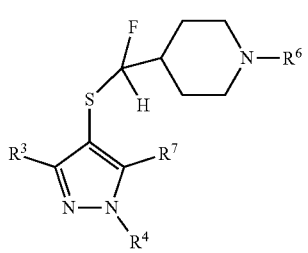

Formula IV comprising the steps of:

a) fluorinating a compound of formula V,

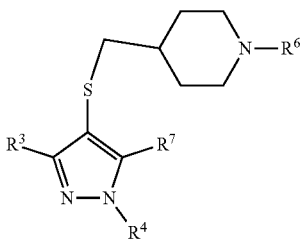

Formula V to obtain a compound of formula IV.

wherein $R^3$, $R^4$, $R^6$ and $R^7$ are as defined above.

In another aspect, the present invention provides a process for preparation of a compound of formula III,

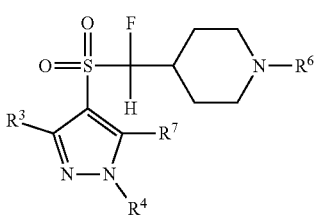

Formula III comprising the steps of:

a) oxidizing the compound of formula IV

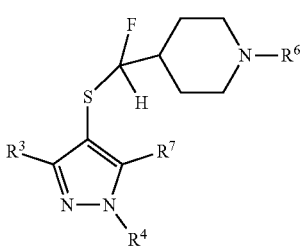

Formula IV to obtain a compound of formula III;

wherein $R^3$, $R^4$, $R^6$ and $R^7$ are as defined above.

In another aspect, the present invention provides a compound of formula VI,

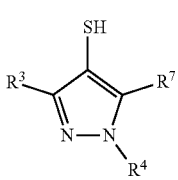

Formula VI wherein $R^3$, $R^4$, $R^7$ and $L_1$ are as defined above.

In another aspect, the present invention provides a process for preparation of a compound of formula V,

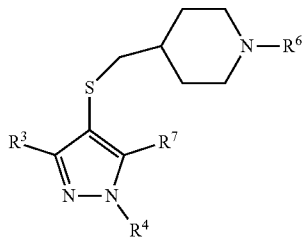

Formula V wherein $R^3$, $R^4$, $R^6$ and $R^7$ are as defined above;
comprising the steps of:
a) reacting the compound of formula VI with a compound of formula VIII,

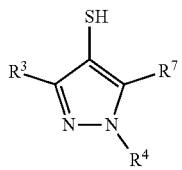

Formula VI

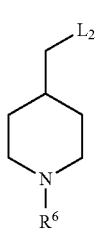

Formula VIII wherein $R^3$, $R^4$ and $R^7$ are as defined above;
to obtain a compound of formula V.

In another aspect, the present invention provides a process for preparation of a compound of formula V,

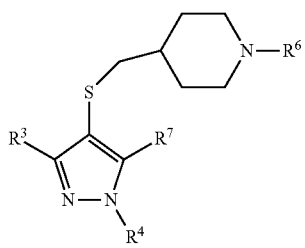

Formula V wherein $R^3$, $R^4$, $R^6$ and $R^7$ are as defined above;
comprising the step of reacting the compound of formula VIB with a compound of formula VIII,

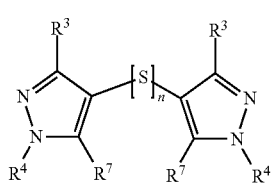

Formula VIB

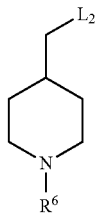

Formula VIII wherein n is 2-8; $R^3$, $R^4$ and $R^7$ are as defined above;
to obtain a compound of formula V.

In another aspect, the present invention provides a compound of formula II and salts thereof.

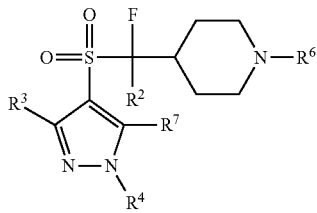

Formula II wherein $R^6$ is H or salt thereof.

In another aspect, the present invention provides a pyrazole compound of formula III

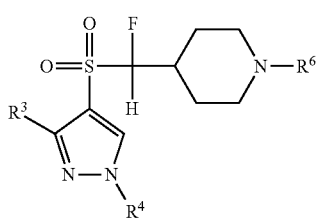

Formula III wherein $R^3$, $R^4$ and $R^6$ are as defined above.

In another aspect, the present invention provides pyrazole compound of formula IV,

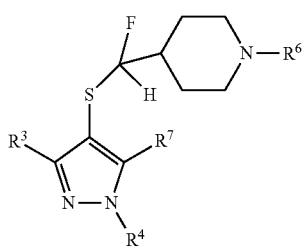

Formula IV wherein $R^3$, $R^4$ and $R^6$ are as defined above.

DETAILED DESCRIPTION OF THE INVENTION

The term "$C_1$-$C_4$ alkyl" in the present invention refers to methyl, ethyl, isopropyl, n-butyl, iso-butyl, tert-butyl, or the like.

The term "$C_1$-$C_4$ haloalkyl" in the present invention refers to alkyl group substituted by one or more halogens. Examples of $C_1$-$C_4$ haloalkyl include, but not limited to fluoromethyl, difluoromethyl, trifluoromethyl, fluoroethyl, difluoroethyl, trifluoroethyl, tetrafluoroethyl, or the like.

The term "$C_1$-$C_4$ alkoxy" in the present invention refers to methoxy, ethoxy, propoxy, isopropoxy, butoxy or the like.

The term "ambient temperature" in the present invention refers to the temperature in the range of 5° C. to 35° C.

The term "heteroaryl" in the present invention refers to 5-6 membered heteroaromatic ring having at least one nitrogen atom as a ring member.

The term "salt" in the present invention refers to hydrochloride, hydrobromide, mesylate, tosylate or the like.

The term "protecting group" in the present invention refers to the groups used in the art and serve the function of blocking amino moiety while the reactions are carried out at other sites of the molecule. Examples of amino protecting groups include, but not limited to acyl, alkoxycarbonyl, alkenyloxycarbonyl and aralkyloxycarbonyl groups such as carbobenzyloxy, tert.-butoxycarbonyl, trityl, pthaloyl, and the like.

The term "deprotection" in the present invention refers to the process of removal of protecting group. The step of deprotection is carried out by a procedure known in the art or as described in Protecting Groups by Carey & Sundberg, which is included as a reference. The step can be carried out using an acid such as hydrochloric acid, hydrobromic acid, acetic acid or trifluoroacetic acid, or a base such as sodium hydroxide or potassium hydroxide.

The term "leaving group" in the present invention refers to an atom or a group of atoms which can be displaced during the reaction. The leaving group includes but are not limited to organosulphonyl groups, acyloxy groups, alkoxy groups, alkoxy carbonyl groups (e.g., ethoxy carbonyl or the likes); halogens (e.g., iodine, bromine, chlorine or fluorine); amido; azido; isocyanato; substituted or unsubstituted thiolates (e.g., thiomethyl or thiophenyl). The Examples of leaving groups include mesyl, tosyl, bromo, iodo, and the like.

A catalyst, used in the step of formation of compound of formula VI/VIB/VIC, is selected from the salts of copper or iron. The catalyst includes copper chloride (CuCl), copper bromide (CuBr), copper iodide (CuI), iron chloride ($FeCl_3$), Iron bromide ($FeBr_3$) or the like.

The term "reducing agent" in the present invention refers to Zinc/acetic acid, Zinc/alcoholic potassium hydroxide, sodium borohydride, potassium borohydride, lithium aluminum hydride, triphenylphosphine/HCl, and tris(2-carboxyethyl)phosphine, borane, triphenylphosphine, tributylphosphine, tris(2-carboxyethyl)phosphine, or the like.

The term "base" in the present invention refers to inorganic or organic bases.

Examples of inorganic bases include potassium carbonate, sodium carbonate, cesium carbonate, sodium bicarbonate, sodium hydride, potassium hydride, or the like. Examples of organic bases includes sodium ethoxide, sodium methoxide, lithium tert-butoxide, sodium tert-butoxide, potassium tert-butoxide, triethylamine, n-butylamine, t-butylamine, pyridine, methyl lithium, n-butyl lithium, lithium diisopropylamide, lithium 2,2,6,6-tetramethylpziperidine, sodium bis(trimethylsilyl)amide, lithium bis(trimethylsilyl)amide, potassium bis(trimethylsilyl)amide, lithium diethylamide or the like.

The step of fluorination in the present invention is carried out in presence of electrophilic fluorinating agents. Examples of electrophilic fluorinating agents includes N-fluoro-o-benzenedisulfonimide, N-fluorobenzenesulfonimide, 1-chloromethyl-4-fluoro-1,4-diazoniabicyclo[2.2.2]octane bis(tetrafluoroborate), N-fluoro-pyridinium salts such as 1-fluoropyridinium triflate, 1-fluoropyridinium tetrafluoroborate, 1-fluoro-2,4,6-trimethylpyridinium tetrafluoroborate, 1-Fluoro-2,4,6-trimethylpyridinium triflate, 1-fluoro-2,6-dichloropyridinium triflate, 2,6-dichloro-1-fluoropyridinium tetrafluoroborate, 2-fluoro-1,3-dimethylpyridinium p-toluenesulfonate, 2-fluoro-1-methylpyridinium p-toluenesulfonate, N-fluoro-N'-(chloromethyl)triethylene diamine bis(tetrafluoroborate). Preferably, the fluorinating agents are selected from a group consisting of 1-fluoropyridinium triflate, 1-fluoropyridinium tetrafluoroborate, 1-fluoro-2,4,6-trimethylpyridinium tetrafluoroborate, 1-fluoro-2,4,6-trimethylpyridiniumtriflate, 1-fluoro-2,6-dichloropyridinium triflate, 2,6-dichloro-1-fluoropyridinium tetrafluoroborate, 1-fluoro-4-methylpyridinium triflate, 1-fluoro-4-methylpyridinium tetrafluoroborate. The step of oxidation is carried out using an oxidant, optionally in the presence of a catalyst to oxidize sulfide to sulfone. Examples of the oxidant includes hydrogen peroxide/sodium tungstate, peracetic acid, benzyl hydroperoxide, ethylbenzene hydroperoxide, cumyl hydroperoxide, sodium hypochlorite, oxalic acid dihydrate/hydrogen peroxide ($H_2O_2$), meta-chloroperoxybenzoic acid (mCPBA), urea-hydrogen peroxide adduct, Permanganate/manganese dioxide, Ruthenium chloride hydrate/sodium periodate, oxone, and the like, optionally in the presence of catalyst, for example, ammonium molybdate or alkali metal tungstate.

The step of alkylation is carried out using alkylating gent in the presence of a base.

The alkylating agent includes but is not limited to bromoalkane, chloroalkane, iodoalkane, diazoalkane, dialkylcarbonate, dialkylsulfonate, and the like.

In an embodiment, the present invention provides a process for preparation of a compound of formula II,

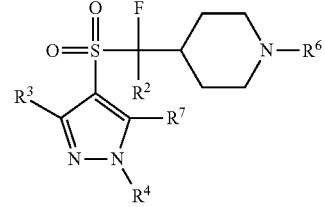

Formula II $R^2$ is independently selected from F, $C_1$-$C_4$ alkyl, $C_1$-$C_4$ haloalkyl; and $R^3$ is selected from H, F, $C_1$-$C_4$ alkyl, C1-C4 haloalkyl, $R^4$ is $C_1$-$C_4$ alkyl, $R^6$ is H or a protecting group or salt thereof and $R^7$ is selected from H, Cl or trialkylsilyl;

comprising the steps of:
a) reacting a compound of formula VII with elemental sulfur in presence of base and a catalyst to give a compound of formula VIB,

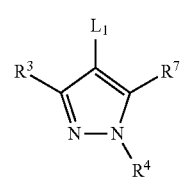

Formula VII

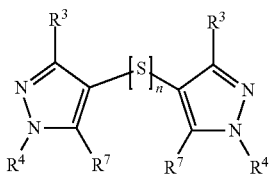
Formula VIB wherein R³ and R⁴ are as defined above, $L_1$ is a leaving group, n is 2-8;
b) reacting the compound of formula VIB with a compound of formula VIII to give a compound of formula V;

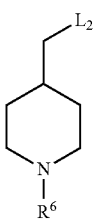
Formula VIII

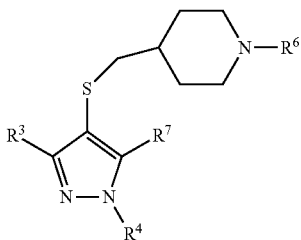
Formula V wherein R⁶ is as defined above, $L_2$ is a leaving group,
c) fluorinating a compound of formula V to give a compound of formula IV;
d) oxidizing a compound of formula IV to give a compound of formula III;
e) alkylating a compound of formula III to give a compound of formula II.

In a specific embodiment, the present invention provides a process for preparation of a compound of formula II, wherein R² and R⁴ represent methyl and R³ represents difluoromethyl.

In a specific embodiment, the present invention provides a process for preparation of a compound of formula II, converting a compound of formula VI or VIB to a compound of formula V; fluorinating the compound of formula V to a compound of formula IV followed by oxidizing the compound of formula IV to a compound of formula III, wherein in compounds of formulae II, V, IV, and III, R² and R⁴ represent methyl and R³ represents difluoromethyl and are represented as the compounds of formulae IIA, VIA, VIC, VA, IVA and IIIA respectively.

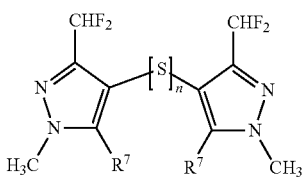
Formula VIC

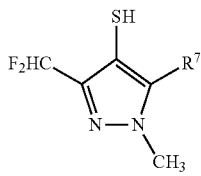
Formula VIA

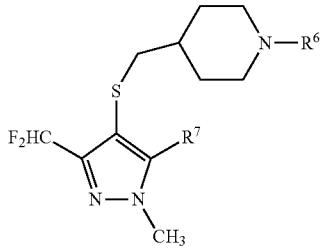
Formula VA

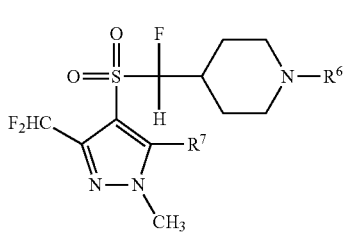
Formula IVA

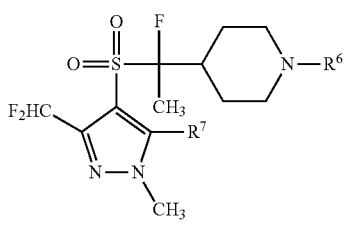
Formula IIIA

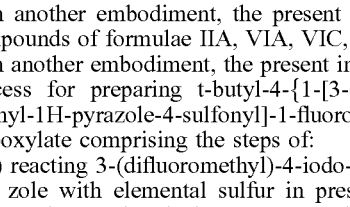
Formula IIA

In another embodiment, the present invention provides compounds of formulae IIA, VIA, VIC, VA, IVA and IIIA.

In another embodiment, the present invention provides a process for preparing t-butyl-4-{1-[3-(difluoromethyl)-1-methyl-1H-pyrazole-4-sulfonyl]-1-fluoroethyl}piperidine carboxylate comprising the steps of:
a) reacting 3-(difluoromethyl)-4-iodo-1-methyl-1H-pyrazole with elemental sulfur in presence of a base, a catalyst and reducing agent to obtain 3-(difluoromethyl)-1-methyl-1H-pyrazole-4-thiol;
b) reacting 3-(difluoromethyl)-1-methyl-1H-pyrazole-4-thiol with tert-butyl 4-{[(methanesulfonyl)oxy]methyl}piperidine-1-carboxylate to give tert-butyl 4-({[3-(difluoromethyl)-1-methyl-1H-pyrazol-4-yl]sulfanyl}methyl)piperidine-1-carboxylate;
c) converting tert-butyl 4-({[3-(difluoromethyl)-1-methyl-1H-pyrazol-4-yl]sulfanyl}methyl)piperidine-1-carboxylate to t-butyl-4-{1-[3-(difluoromethyl)-1-methyl-1H-pyrazole-4-sulfonyl]-1-fluoroethyl}piperidine carboxylate.

In another embodiment, present invention provides a process for preparing t-butyl-4-{1-[3-(difluoromethyl)-1-methyl-1H-pyrazole-4-sulfonyl]-1-fluoroethyl}piperidine carboxylate comprising the steps of:
  a) reacting 3-(difluoromethyl)-4-iodo-1-methyl-1H-pyrazole with elemental sulfur in presence of a base, and a catalyst to obtain 4,4'-disulfanediylbis[3-(difluoromethyl)-1-methyl-1H-pyrazole];
  b) reacting 4,4'-disulfanediylbis[3-(difluoromethyl)-1-methyl-1H-pyrazole] with tert-butyl 4-{[(methanesulfonyl)oxy]methyl}piperidine-1-carboxylate to give tert-butyl-4-({[3-(difluoromethyl)-1-methyl-1H-pyrazol-4-yl]sulfanyl}methyl)piperidine-1-carboxylate;
  c) converting tert-butyl 4-({[3-(difluoromethyl)-1-methyl-1H-pyrazol-4-yl]sulfanyl}methyl)piperidine-1-carboxylate to t-butyl-4-{1-[3-(difluoromethyl)-1-methyl-1H-pyrazole-4-sulfonyl]-1-fluoroethyl}piperidine carboxylate.

In another embodiment of the present invention the step a) of reacting a compound of formula VII with sulfur is carried out in the presence of a base selected from a group consisting of potassium carbonate, sodium carbonate, cesium carbonate or the like.

In another embodiment the present invention, step a) of reacting a compound of formula VII with a sulfur is optionally carried out in the presence an additive agent, selected from a group that includes potassium iodide, sodium iodide or dimethylaminopyridine (DMAP) or the like.

In another embodiment of the present invention, the step a) of reacting a compound of formula VII with a sulfur is carried out in a solvent. EXAMPLEs of solvents includes dimethylformamide, dimethylacetamide, ethyl methyl ketone, acetone, methyl isopropyl ketone, methyl isobutyl ketone, methyl n-butyl ketone, methyl t-butyl ketone, methyl isoamyl ketone, dimethyl sulfoxide, sulfolane, hexamethylphosphoric triamide, tetrahydrofuran, dioxane, dimethoxyethane, diethylene glycol, dimethyl ether, diethylether, dichloromethane, dichloroethane, chloroform, carbon tetrachloride, toluene, ethyl acetate, acetonitrile, or mixture(s) thereof.

In another embodiment of the present invention, the step a) of reacting a compound of formula VII with a sulfur is carried out in presence of a reducing agent selected from a group consisting of triphenylphosphine, tributylphosphine, tris(2-carboxyethyl)phosphine, or the like.

In another embodiment of the present invention, the step b) of reacting a compound of formula VI/VIA/VIB with a compound of formula VIII is carried out in presence of base.

In another embodiment of the present invention, the reaction does not involve isolation of the compound of formula VI or VIA.

In another embodiment of the present invention, the reaction does not involve isolation of the compound of formula VI or VIA.

In another embodiment, the step of fluorination is carried out in presence of an electrophilic fluorinating agent.

In another embodiment, the step of fluorination is carried out in the presence of N-fluoro-pyridinium salts.

In another embodiment of the present invention, the compound of formula IVA may not be isolated.

In another embodiment of the present invention, the compound of formula IIIA may not be isolated.

In another embodiment of the present invention, the step of oxidation may precede step of fluorination.

In another embodiment of present invention, it provides a process for preparation tert-butyl-4-{1-[3-(difluoromethyl)-1-methyl-1H-pyrazole-4-sulfonyl]-1-fluoroethyl}piperidine-1-carboxylate comprising the steps of:
  a) fluorinating tert-butyl-4-({[3-(difluoromethyl)-1-methyl-1H-pyrazol-4-yl]sulfanyl}methyl)piperidine-1-carboxylate in presence of N-fluoro-pyridinium salts to obtain tert-butyl 4-[{[3-(difluoromethyl)-1-methyl-1H-pyrazol-4-yl]sulfanyl}(fluoro)methyl]piperidine-1-carboxylate;
  b) oxidizing tert-butyl-4-[{[3-(difluoromethyl)-1-methyl-1H-pyrazol-4-yl]sulfanyl}(fluoro)methyl]piperidine-1-carboxylate to tert-butyl-4-{1-[3-(difluoromethyl)-1-methyl-1H-pyrazole-4-sulfonyl]-1-fluoromethyl}piperidine-1-carboxylate.
  c) converting tert-butyl-4-{1-[3-(difluoromethyl)-1-methyl-1H-pyrazole-4-sulfonyl]-1-fluoromethyl}piperidine-1-carboxylate to tert-butyl-4-{1-[3-(difluoromethyl)-1-methyl-1H-pyrazole-4-sulfonyl]-1-fluoroethyl}piperidine-1-carboxylate.

In another embodiment of present invention, present invention provides a process that does not involve isolation of either tert-butyl-4-[{[3-(difluoromethyl)-1-methyl-1H-pyrazol-4-yl]sulfanyl}(fluoro)methyl]piperidine-1-carboxylate or 4-{[3-(difluoromethyl)-1-methyl-1H-pyrazole-4-sulfonyl](fluoro)methyl}piperidine-1-carboxylate.

In another embodiment of this aspect, the present invention provides a process for preparation tert-butyl-4-{1-[3-(difluoromethyl)-1-methyl-1H-pyrazole-4-sulfonyl]-1-fluoroethyl}piperidine-1-carboxylate, wherein, the step of fluorination and oxidation occurs without isolation of tert-butyl 4-[{[3-(difluoromethyl)-1-methyl-1H-pyrazol-4-yl]sulfanyl}(fluoro)methyl]piperidine-1-carboxylate.

In an embodiment of present invention, it provides a process for preparation of a compound of formula IIA,

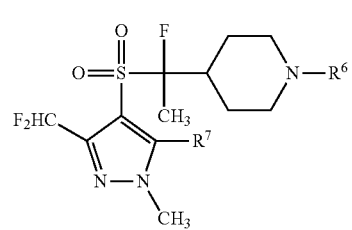

Formula IIA wherein $R^6$ and $R^7$ are as defined above, comprising the steps of:
  a) methylating the compound of formula IIIA,

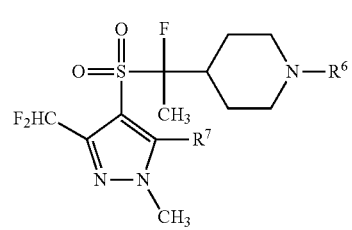

Formula IIIA

In another embodiment, present invention involves a step of hydrolysis of compound of formula IIA, wherein $R^7$ is Cl or alkylsilyl group, to a compound of formula IIA, wherein $R^7$ is hydrogen.

In another embodiment, present invention involves a step of de-protection of the compound of formula IIA, wherein $R^6$ is a protecting group, to a compound of formula IIA, wherein $R^6$ is hydrogen.

In an embodiment, present invention provides a compound of formula IIB and salts thereof in purity of 95% to 99%.

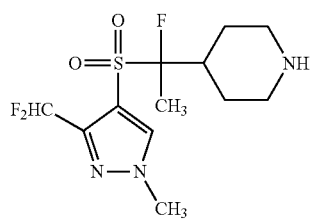

Formula IIB

In another embodiment, present invention provides 4-{1-[3-(difluoromethyl)-1-methyl-1H-pyrazole-4-sulfonyl]-1-fluoroethyl}piperidine and salts thereof.

In an embodiment, present invention provides a process for using a compound of formula IIB or salt thereof for preparation of compound of formula I.

In another embodiment, present invention involves isolation of a compound of formula IIC as a solid compound,

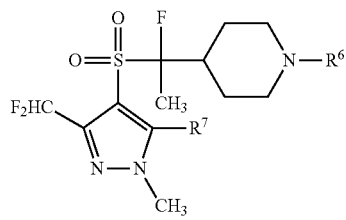

Formula IIC wherein $R^6$ is tert-butyloxycarbonyl and $R^7$ is hydrogen.

The compound of formula IIC is isolated in crystalline and/or amorphous form. The isolation of the compound of formula IIC is carried out using crystallization in a suitable solvent or mixture of solvents at a temperature of about −20° C. to 30° C.

The solvents used in the crystallization can be selected from the group consisting of methanol, ethanol, propanol, 2-propanol, tetrahydrofuran, acetonitrile, cyclohexane, hexane, heptane, toluene, water or the like and the mixture thereof.

In an embodiment, present invention provides a pyrazole compound of formula IIIA,

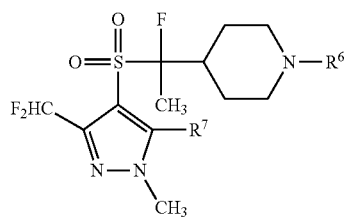

Formula IIIA wherein $R^6$ is as defined above.

In another embodiment, present invention provides tert-butyl-4-{[3-(difluoromethyl)-1-methyl-1H-pyrazole-4-sulfonyl](fluoro)methyl}piperidine-1-carboxylate.

In another embodiment, present invention provides a process for using a compound of formula IIIA for preparation of compound of formula I.

An aspect of the present invention provides compound of formulae II, IIA, IIB, IIC, III and/or IIIA as impurity in the compound of formula I.

The compound of formulae II and III can be converted to the compound of formula I using the methods known or taught in WO 2016118774, which is included as a reference.

In another embodiment, present invention provides a process for preparation of compound of formula II, wherein the process does not involve isolation of the intermediate of formula VIB.

The process for conversion of a compound of formula V to a compound of formula II involves the step of fluorination, followed by oxidation and subsequent alkylation or permutation and combination of these steps to give a compound of formula II.

In a particular Example, tert-butyl 4-({[3-(difluoromethyl)-1-methyl-1H-pyrazol-4-yl]sulfanyl}methyl)piperidine-1-carboxylate is fluorinated using an electrophilic fluorinating agent to yield tert-butyl-4-{[3-(difluoromethyl)-1-methyl-1H-pyrazole-4-sulfonyl](fluoro)methyl}piperidine-1-carboxylate, which upon oxidation and subsequent methylation yields tert-butyl-4-{1-[3-(difluoromethyl)-1-methyl-1H-pyrazole-4-sulfonyl]-1-fluoroethyl}piperidine-1-carboxylate. Tert-butyl-4-{1-[3-(difluoromethyl)-1-methyl-1H-pyrazole-4-sulfonyl]-1-fluoroethyl}piperidine-1-carboxylate upon de-protection gives 4-{1-[3-(difluoromethyl)-1-methyl-1H-pyrazole-4-sulfonyl]-1-fluoroethyl}piperidine.

The compounds of formulae II, III, IV, and V can be used for preparation of compound of formula I.

The compounds of formulae V and VA can be converted to a compound of formula II, by the methods taught in WO 2016118774 which are included as reference.

The compounds of formula II can be converted to the compound of formula I using the methods known or taught in WO 2016118774, which is included as a reference.

The compound of formula VII and VIII, used as starting material can either be obtained commercially or be prepared by the method as disclosed in PCT Pub. No. 2009/000442 and US Pub. No. 2010/29650. The compound of formula VIB can also be obtained commercially or can be prepared by the method as disclosed in Chinese Pub. No. 105622469. Pyrazole carboxylic acid used as a raw material can either be obtained commercially or be prepared by the method described in U.S. Pat. No. 9,650,345. These patent references have been cited as references in the present invention.

In a particular embodiment, the present invention provides a process for preparation of 3-(difluoromethyl)-4-iodo-1-methyl-1H-pyrazole comprising the step of decarboxylation of 3-(difluoromethyl)-1-methyl-1H-pyrazole-4-carboxylic acid using Cu powder and Cu2O in presence of aliphatic amine in polar aprotic solvent followed by the step of iodination of 3-(difluoromethyl)-1-methyl-1H-pyrazole using iodine and potassium iodate in presence of acetic acid and sulphuric acid. Examples of aliphatic amine include methylamine, ethylamine, triethylamine, diethylmethylamine, isopropylamine, disopropylamine, diisopropylmethylamine, diisopropylethylamine, n-butylamine, tertiary butylamine, tributylamine, or the like.

Another aspect of the present invention provides a process for preparation of a compound of formula Z,

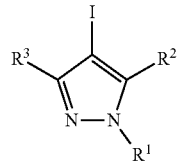

(Z)

wherein R¹ is hydrogen, $C_1$-$C_6$ alkyl optionally substituted with one or more halogen atoms, $C_3$-$C_6$ cycloalkyl, or arylalkyl;

R² is hydrogen, $C_1$-$C_6$ alkyl, $C_3$-$C_6$ cycloalkyl, arylalkyl, or aryl.

R³ is $C_1$-$C_6$ alkyl substituted with one or more halogen atoms;

wherein each halogen atom is independently selected from fluorine, chlorine, bromine, and iodine;

comprising the steps of:

a) decarboxylating a compound of formula X using a copper reagent in the presence of an aliphatic amine to obtain a compound of formula Y; and

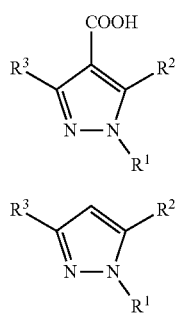

b) iodinating the compound of formula Y to obtain the compound of formula Z.

The term "copper reagent" in the present invention refers to copper powder, cuprous oxide, cupric oxide, copper chloride, and copper iodide, or mixtures thereof.

The term "aliphatic amine" in the present invention refers to straight chain or branched chain alkyl amine, Examples of aliphatic amine include methylamine, ethylamine, triethylamine, diethylmethylamine, isopropylamine, diisopropylamine, diisopropylmethylamine, diisopropylethylamine, n-butylamine, tertiary butylamine, tributylamine, or the like.

The term "organic acid" in the present invention refers to lower alkyl sulfonic acids as well as arylsulfonic acids and carboxylic acids. Examples of organic acid includes acetic acid, oxalic acid, pyruvic acid, benzoic acid, methanesulfonic acid, benzenesulfonic acid, p-toluenesulfonic acid, or the like.

In an embodiment of the present invention, the step of decarboxylation involves use of copper powder, cuprous oxide, copper powder in the presence of tributyl amine, triethylamine, diisopropylethylamine or diisopropylmethylamine, or a mixture thereof.

In an embodiment of the present invention, the step of decarboxylation is carried out in the presence of copper oxide, copper powder, or a mixture thereof at a temperature of about 130° C. to 230° C.

In another embodiment of the present invention, the aliphatic amine is recycled back into the reactor, e.g., for continuous decarboxylation.

In another embodiment of the present invention, the step of decarboxylation is carried out in a polar aprotic solvent. Examples of polar aprotic solvents include acetone, methyl ethyl ketone, ethyl acetate, N,N-dimethylformamide, acetonitrile, dimthylsulfoxide, N,N-dimethylacetamide, sulfolane, dimethoxyethane, dioxane or the like.

In a preferred embodiment of the present invention, the step of decarboxylation is carried out in sulfolane.

In an embodiment of the present invention, the step of iodination is carried out in the presence of an organic acid.

In an embodiment of the present invention, the step of iodination is carried out using iodine and potassium iodate in the presence of an organic acid.

In another embodiment of the present invention, the step of iodination is carried out using iodine in presence of potassium iodate, sulfuric acid and acetic acid at a temperature of about 20° C. to 100° C.

In another preferred embodiment of the present invention, the step of iodination is carried out using iodine and potassium iodate in the presence of acetic acid.

In a particular embodiment, the present invention provides a process for preparation of 3-(difluoromethyl)-1-methyl-1H-pyrazole comprising the step of decarboxylation of 3-(difluoromethyl)-1-methyl-1H-pyrazole-4-carboxylic acid using copper powder and copper oxide in the presence of tributyl amine in sulfolane.

In another particular embodiment, the present invention provides a process for preparation of 3-(difluoromethyl)-4-iodo-l-methyl-1H-pyrazole comprising the step of iodination of 3-(difluoromethyl)-1-methyl-1H-pyrazole using iodine and potassium iodate in the presence of acetic acid and sulphuric acid.

Embodiments of the invention are not mutually exclusive, but may be implemented in various combinations. The described embodiments of the invention and the disclosed examples are given for the purpose of illustration rather than limitation of the invention as set forth in the appended claims.

The following example is given by way of illustration and therefore should not be construed to limit the scope of the present invention.

EXAMPLES

Example 1: Preparation of 3-(difluoromethyl)-1-methyl-1H-pyrazole

Tributylamine (90 gm, 0.48 mol) was added to a mixture of 3-(difluoromethyl)-1-methyl-1H-pyrazole-4-carboxylic acid (170 gm, 0.966 mol), Cu Powder (10.8 gm, 0.176 mol), and $Cu_2O$ (9.67 gm, 0.067 mol) in sulfolane (252 gm, 2.1 mol) at ambient temperature. The reaction mixture was stirred at 150° C. for six hours. After completion of the reaction, the product is distilled off from the reaction under vacuum. Tributylamine was recycled back to the reactor.

Yield: 80% Purity: 95%.

Example 2: Preparation of 3-(difluoromethyl)-4-iodo-1-methyl-1H-pyrazole

Sulfuric acid (98%; 64.37 g) was dropwise added to a mixture of 3-(difluoromethyl)-1-methyl-1H-pyrazole (73.5 g, 0.56 mol), Iodine (67.5 g, 0.27 mol), potassium iodate (31 g, 0.14 mol) and acetic acid (816 g) at about 45° C. in about 20 minutes. The temperature of the reaction mixture was raised to a temperature of about 60° C. and maintained at the same temperature for an hour. The reaction mixture was quenched with water (500 ml) at about 25° C. to about 30° C., the mixture was neutralized with an aqueous solution of sodium bisulfite (100 ml). The mixture was extracted with dichloromethane (200 ml). The layers were separated and washed twice with water (500 ml). The organic layers were combined and concentrated to give 3-(difluoromethyl)-4-iodo-1-methyl-1H-pyrazole.

Yield: 90%; Purity: 96%

Example 3: Preparation of 3-(difluoromethyl)-1-methyl-1H-pyrazole-4-thiol 3-(Difluoromethyl)-4-iodo-1-methyl-1H-pyrazole (50 g) was added to mixture of potassium carbonate (52 g), copper iodide (3.56 g), sulfur powder (18.2 g) in dimethylformamide (250 ml) at a temperature of about 50° C. in 10 to 20 minutes. The reaction mixture was stirred at a temperature of about 110° C. for 4 to 5 hours. The reaction mixture was allowed cooled to a temperature of about 20° C. A mixture of triphenylphosphine (125 g), in water (125 ml) and dioxane (325 ml), was added to the reaction mixture. Hydrochloric acid (35%; 42 ml) was slowly added to the reaction mass while maintaining the temperature of reaction mixture to below 30° C. After completion of the addition, the reaction mixture was stirred at a temperature of about 40° C. The reaction mixture was concentrated at a temperature of about 80° C. to obtain a residue. Water (700 ml) and dichloromethane (150 ml) were added to the residue and stirred for about 15 minutes. The pH of the mixture was adjusted to 4.5-5 and layers were separated. Aqueous layer was again extracted with dichloromethane (60 ml). The organic layers were combined and filtered and washed with water. A solution of potassium hydroxide (20%; 80 ml) was added to the organic layer. The organic layer was washed with water, passed through sodium sulfate bed and concentrated to obtain the desired compound.

Yield: 65%; Purity: 93%

Example 4: Preparation of 3-(difluoromethyl)-1-methyl-1H-pyrazole-4-thiol 3-(Difluoromethyl)-4-iodo-1-methyl-1H-pyrazole (50 g) was added to mixture of sodium carbonate (52 g), copper iodide (3.56 g), sulfur powder (18.2 g) in dimethylsulfoxide (250 ml) at a temperature of about 50° C. in 10 to 20 minutes. The reaction work up was done as per the example 3.

Yield: 60%; Purity: 93%

Example 5: Preparation of 3-(difluoromethyl)-1-methyl-1H-pyrazole-4-thiol 3-(Difluoromethyl)-4-iodo-1-methyl-1H-pyrazole (50 g) was added to mixture of sodium methoxide (30 g), copper iodide (3.56 g), sulfur powder (18.2 g) in sulfolane (250 ml) at a temperature of about 50° C. in 10 to 20 minutes. The reaction mixture was stirred at a temperature of about 110° C. for 4 to 5 hours. The reaction work up was proceeded as per the example 3.

Yield: 60%; Purity: 93%

Example 6: Preparation of 3-(difluoromethyl)-1-methyl-1H-pyrazole-4-thiol 3-(Difluoromethyl)-4-iodo-1-methyl-1H-pyrazole (50 g) was added to mixture of potassium carbonate (52 g), copper iodide (3.56 g), sulfur powder (18.2 g) in sulfolane (250 ml) at a temperature of about 50° C. in 10 to 20 minutes. The reaction mixture was stirred at a temperature of about 110° C. for 4 to 5 hours. The reaction was proceeded as per the example 3.

Yield: 65%; Purity: 93%

Example 7: Preparation of tert-butyl 4-({[3-(difluoromethyl)-1-methyl-1H-pyrazol-4-yl]sulfanyl}methyl)piperidine-1-carboxylate 3-(difluoromethyl)-1-methyl-1H-pyrazole-4-thiol (13 g) was added to a mixture of tert-butyl 4-{[(methanesulfonyl)oxy]methyl}piperidine-1-carboxylate (20 g) and potassium carbonate (20.6 g) in acetonitrile (200 ml). The reaction mixture was stirred at a temperature of 60° C. for one hour. The progress of the reaction was monitored by gas chromatography. After completion of reaction, the reaction was cooled to room temperature and filtered. The filtered mass was washed with dichloromethane (100 ml). The organic layer was washed with a dilute solution of hydrochloric acid (1N; 200 ml). The organic layer was concentrated to obtain the title compound.

Yield: 70%; Purity: 97%

Example 8: Preparation of tert-butyl 4-({[3-(difluoromethyl)-1-methyl-1H-pyrazol-4-yl]sulfanyl}methyl)piperidine-1-carboxylate 3-(difluoromethyl)-1-methyl-1H-pyrazole-4-thiol (13 g) was added to a mixture of tert-butyl 4-{[(methanesulfonyl)oxy]methyl}piperidine-1-carboxylate (20 g) and sodium methoxide (15 g) in acetonitrile (200 ml). The reaction mixture was stirred at a temperature of 60° C. for one hour. The reaction was proceeded as per the example 8.

Yield: 70%; Purity: 97%

Example 9: Preparation of 4,4'-disulfanediylbis[3-(difluoromethyl)-1-methyl-1H-pyrazole]

3-(Difluoromethyl)-4-iodo-1-methyl-1H-pyrazole (50 g) was added to a mixture of potassium carbonate (52.6 g), copper iodide (3.56 g) and sulfur powder (18.25 g) in dimethylformamide (DMF, 400 g). The reaction mixture was heated to a temperature of 110° C. and stirred for 3 to 4 hours at the same temperature. The progress of the reaction was monitored by Gas chromatography (GC). The reaction mixture was concentrated at a temperature of about 80° C. using reduced pressure of about 50 mbar to obtain a residue. Dichloromethane (150 ml) was added to the residue and filtered through hyflo super cell. The filter cake was washed with dichloromethane (150 ml). Organic layer was washed with water (500 ml×2). The organic layer was concentrated to obtain the desired product. GCMS 326+

Example 10: Preparation of 4,4'-disulfanediylbis-[3-(difluoromethyl)-1-methyl-1H-pyrazole]

3-(Difluoromethyl)-4-iodo-1-methyl-1H-pyrazole (50 g) was added to a mixture of potassium carbonate (52.6 g), copper iodide (3.56 g) and sulfur powder (18.25 g) in sulfolane (400 g). The reaction mixture was proceeded as per example 9. GCMS 326+

Example 11: Preparation of tert-butyl 4-({[3-(difluoromethyl)-1-methyl-1H-pyrazol-4-yl]sulfanyl}methyl)piperidine-1-carboxylate using 4,4'-disulfanediylbis[3-(difluoromethyl)-1-methyl-1H-pyrazole]

Sodium borohydride (1.78 g) was slowly added to a mixture of 4,4'-disulfanediylbis[3-(difluoromethyl)-1-methyl-1H-pyrazole (7.4 g), tert-butyl 4-{[(methanesulfonyl)oxy]methyl}piperidine-1-carboxylate (9.7 g), potassium carbonate (12.2 g) in acetonitrile (100 ml) at a temperature of 20° C. The reaction mixture was stirred at a temperature of about 60° C. for 1 hour. The progress of the reaction was monitored using GC. After completion of the reaction, the reaction mass was filtered. The residue was washed with dichloromethane (100 ml). The filtrate was concentrated to obtain a residue. Dichloromethane (100 ml) and water was added to the residue. The organic layer was washed with a dilute solution of hydrochloric acid (1N, 200 ml). Organic layer was concentrated to give the desired product.

Example 12: Preparation of tert-butyl-4-{[3-(difluoromethyl)-1-methyl-1H-pyrazole-4yl]sulfanyl](fluoro)methyl}piperidine-1-carboxylate 1-Fluoro-2, 4, 6-tri-methyl pyridinium triflate (0.8648 mmol) was added to solution of tert-butyl-4-({[3-(difluoromethyl)-1-methyl-1H-pyrazol-4-yl]sulfanyl}methyl)piperidine-1-carboxylate (0.8648 mmol) in dichloromethane (15 ml) at a temperature of about 30 to 35° C. under nitrogen atmosphere. The reaction mass was refluxed at 40° C. for 10-11 hours. The progress of the reaction was monitored by high performance liquid chromatography (HPLC). The reaction mixture was cooled to 0° C. A solution of ruthenium chloride hydrate (0.012 mmol) in tetrahydrofuran (6 ml) was added to the reaction mixture at 0° C. The progress of the reaction was monitored with HPLC. After completion of reaction, mixture was quenched by water. The layers were separated, filtered and concentrated to isolate the tert-butyl-4-{[3-(difluoromethyl)-1-methyl-1H-pyrazole-4yl]sulfanyl}(fluoro)methyl)piperidine-1-carboxylate. GCMS: 402 [M+Na]⁺

Yield: 85%; Purity: 95%

Example 13: Preparation of tert-butyl-4-{[3-(difluoromethyl)-1-methyl-1H-pyrazole-4yl]sulfanyl}(fluoro)methyl)piperidine-1-carboxylate 2,6-Dichloro-1-fluoropyridiniumtetrafluoroborate (0.9 mmol) was added to solution of tert-butyl-4-({[3-(difluoromethyl)-1-methyl-1H-pyrazol-4-yl]sulfanyl}methyl)piperidine-1-carboxylate (0.8648 mmol) in dichloromethane (15 ml) at a temperature of about 30 to 35° C. under nitrogen atmosphere. The reaction mass was refluxed at 40° C. for 10-11 hours. The progress of the reaction was monitored by high performance liquid chromatography (HPLC). The reaction mixture was cooled to 0° C. A solution of ruthenium chloride hydrate (0.012 mmol) in tetrahydrofuran (6 ml) was added to the reaction mixture at 0° C. The progress of the reaction was monitored with HPLC. After completion of the reaction, the mixture was quenched by water. Layers were separated, filtered and concentrated to isolate tert-butyl-4-{[3-(difluoromethyl)-1-methyl-1H-pyrazole-4yl]sulfanyl}(fluoro)methyl)piperidine-1-carboxylate. GCMS: 402 [M+Na]⁺

Yield: 80%; Purity: 90%

Example 14: Preparation of tert-butyl-4-{[3-(difluoromethyl)-1-methyl-1H-pyrazole-4-sulfonyl](fluoro)methyl}piperidine-1-carboxylate Sodium meta periodate (3.44 mmol) in water was added to the reaction mixture containing tert-butyl-4-{[3-(difluoromethyl)-1-methyl-1H-pyrazole-4yl]sulfanyl}(fluoro)methyl)piperidine-1-carboxylate (1.5 mmol) in tetrahydrofuran (6 ml) at 0° C. The reaction mixture was stirred for 1-2 hour at 0° C. The reaction mass was quenched with water (15 ml) and extracted with dichloromethane (10 ml). The resultant two phase mixture was separated using a separating funnel and the aqueous layer was extracted twice with dichloromethane (10 ml). The organic layers were combined and washed with water (10 ml). The final organic layer was concentrated to get the title compound. The product was analysed by HPLC chromatography. MS (ES, m/z): 434 [M+Na]+

Yield: 90%; Purity: 95%

Example 15: Preparation of tert-butyl-4-{[3-(difluoromethyl)-1-methyl-1H-pyrazole-4-sulfonyl](fluoro)methyl}piperidine-1-carboxylate 1-Fluoro-2, 4, 6 tri methyl pyridinium triflate (0.8648 mmol) was added to solution of tert-butyl-4-({[3-(difluoromethyl)-1-methyl-1H-pyrazol-4-yl]sulfanyl}methyl)piperidine-1-carboxylate (0.8648 mmol) in dichloromethane (15 ml) at a temperature of about 30 to 35° C. under nitrogen atmosphere. The reaction mass was refluxed at 40° C. for 10-11 hours. The progress of the reaction was monitored by high performance liquid chromatography (HPLC). The reaction mixture was cooled to 0° C. A solution of ruthenium chloride hydrate (0.012 mmol) in tetrahydrofuran (6 ml) was added to the reaction mixture at 0° C. Sodium meta periodate (3.44 mmol) in water was added to the reaction mixture maintaining the temperature at 0° C. The reaction mixture was stirred for 1-2 hour at 0° C. The reaction mass was quenched with water (15 ml) and extracted with dichloromethane (10 ml). The resultant two phase mixture was separated using a separating funnel and the aqueous layer was extracted twice with dichloromethane (10 ml). The organic layers were combined and washed with water (10 ml). The final organic layer was concentrated to get the title compound. The product was analysed by HPLC chromatography. MS(ES, m/z): 434 [M+Na]+

Yield: 80%; Purity: 90%.

Example 16: Preparation of tert-butyl-4-{[3-(difluoromethyl)-1-methyl-1H-pyrazole-4-sulfonyl](fluoro)methyl}piperidine-1-carboxylate 1-Fluoropyridinium triflate (0.9 mmol) was added to a solution of tert-butyl 4-({[3-(difluoromethyl)-1-methyl-1H-pyrazol-4-yl]sulfanyl}methyl)piperidine-1-carboxylate (0.8648 mmol) in dichloromethane (15 ml) at a temperature of about 30 to 35° C. under nitrogen atmosphere. The reaction mass was refluxed at 40° C. for 10-11 hours. The progress of the reaction was monitored by high performance liquid chromatography (HPLC). The reaction mixture was proceeded with oxidation as per the Example 15. MS (ES, m/z): 434 [M+Na]+

Yield: 70%; Purity: 90%

Example 18: Preparation of tert-butyl-4-{[3-(difluoromethyl)-1-methyl-1H-pyrazole-4-sulfonyl](fluoro)methyl}piperidine-1-carboxylate 1-Fluoropyridinium tetrafluoroborate (0.8648 mmol) was added to a solution of tert-butyl4-({[3-(difluoromethyl)-1-methyl-1H-pyrazol-4-yl]sulfanyl}methyl)piperidine-1-carboxylate (0.8648 mmol) in dichloromethane (15 ml) at a temperature of about 30 to 35° C. under nitrogen atmosphere. The reaction mass was refluxed at 40° C. for 10-11 hours. The progress of the reaction was monitored by high performance liquid chromatography (HPLC). The reaction mixture was cooled to 0° C. The reaction mixture was proceeded with oxidation as per the Example 15. MS (ES, m/z): 434 [M+Na]+

Yield: 70%; Purity: 90%

Example 19: Preparation of tert-butyl-4-{[3-(difluoromethyl)-1-methyl-1H-pyrazole-4-sulfonyl](fluoro)methyl}piperidine-1-carboxylate 1-Fluoro-2,4,6-trimethylpyridinium tetrafluoroborate (0.8648 mmol) was added to a solution of tert-butyl 4-({[3-(difluoromethyl)-1-methyl-1H-pyrazol-4-yl]sulfanyl}methyl)piperidine-1-carboxylate (0.8648 mmol) in dichloromethane (15 ml) at a temperature of about 30 to 35° C. under nitrogen atmosphere. The reaction mass was refluxed at 40° C. for 10-11 hours. The progress of the reaction was monitored by high performance liquid chromatography (HPLC). The reaction mixture was cooled to 0° C. The reaction mixture was proceeded with oxidation as per the EXAMPLE 15. MS: 434 [M+Na]+

Yield: 70%; Purity: 85%

Example 20: Preparation of tert-butyl-4-{1-[3-(difluoromethyl)-1-methyl-1H-pyrazole-4-sulfonyl]-1-fluoroethyl}piperidine-1-carboxylate Potassium tertiarybutoxide (1M; 14.6 ml) was dropwise added to a solution of tert-butyl-4-{[3-(difluoromethyl)-1-methyl-1H-pyrazole-4-sulfonyl](fluoro)methyl}piperidine-1-carboxylate (2 gm, 0.0048 mol) in THF (45 ml) under nitrogen atmosphere. The reaction mixture was cooled to −30° C. followed by addition of sodium hydride (0.28 gm, 0.0065 mol) was added to the reaction mixture and stirred for 20 minutes at −30° C. A solution of methyl iodide (0.75 gm, 0.0053 mol) in THF (5 ml) was added to the reaction mixture while maintaining the temperature at −30° C. for 10 min and then stirred for 30 min at −30° C. The reaction was monitored using (HPLC). After completion of the reaction, acetonitrile (50 ml) was added to the reaction mixture and the pH of the reaction mixture was adjusted to 6 using a solution of acetic acid (2 ml). The reaction mixture was concentrated under reduced pressure to obtain a residue. Dichloromethane (20 ml) was added to the residue filtered through hyflo gel. The residue was washed with dichloromethane (4×10 ml). The filtrate was combined and concentrated under reduced pressure to give the desired product. The crude product was recrystallized using ethanol and cyclohexane to get the pure product.

Purity: 99% (HPLC); Yield: 65%.

Example 20: Preparation of tert-butyl-4-{1-[3-(difluoromethyl)-1-methyl-1H-pyrazole-4-sulfonyl]-1-fluoroethyl}piperidine-1-carboxylate LiHMDS (1M; 14.6 ml) was dropwise added to a solution of tert-butyl-4-{[3-(difluoromethyl)-1-methyl-1H-pyrazole-4-sulfonyl](fluoro)methyl}piperidine-1-carboxylate (2 gm, 0.0048 mol) in THF (45 ml) under nitrogen atmosphere. The reaction mixture was cooled to −78° C. and stirred for 20 minutes. A solution of methyl iodide (0.75 gm, 0.0053 mol) in THF (5 ml) was added to the reaction mixture while maintaining the temperature at −78° C. for 10 minutes and then stirred for 30 minutes at −78° C. The reaction was monitored using (HPLC). After completion of the reaction, saturated ammonium chloride (20 ml) and dichloromethane (20 ml) was added. Layers were separated, organic layer was washed with water and was concentrated under reduced pressure to obtain a residue. The residue was crystallized using isopropyl alcohol and cyclohexane.

Yield: 75%; Purity: 99%; (HPLC).

Example 21: Preparation of 4-{1-[3-(difluoromethyl)-1-methyl-1H-pyrazole-4-sulfonyl]-1-fluoroethyl} piperidine Aqueous hydrochloride (3.5N; 24 ml) was added to a solution of tert-butyl-4-{1-[3-(difluoromethyl)-1-methyl-1H-pyrazole-4-sulfonyl]-1-fluoroethyl} piperidine-1-carboxylate (2.5 g) in acetonitrile (10 ml). The reaction mixture was stirred at 70° C. for one hour. The progress of the reaction was monitored by gas chromatography. After completion of the reaction dichloromethane (15 ml) was added to the reaction mixture and layers were separated. The pH of aqueous layer was maintained to 12-13 using 20% NaOH (18 ml) and extracted two times with dichloromethane (25 ml). The organic layer was concentrated to obtain given compound.

Purity: 99%; Yield: 95%

Example 22A: Preparation of 3-(difluoromethyl)-1-methyl-1H-pyrazole

Tributyl amine (TBA) (90g) was added to a mixture of 3-(difluoromethyl)-1-methyl-1H-pyrazole-4-carboxylic acid (170g), copper powder (10.8g), copper oxide (9.67g) in sulfolane (252g) at a temperature of about 20 to 50° C. The reaction mixture was stirred at a temperature of 150° C. During decarboxylation carbon dioxide gas was released and the product mixture was collected in another vessel. The collected product mixture consisted of two layers i.e., lower layer and upper layer. The layers were separated and upper layer which consisted of TBA was recycled back to reactor. Dichloromethane (150ml) was added to the lower layer. The organic layer was washed twice with an aqueous solution of hydrochloric acid solution (1N, 150ml). The layers were separated and the organic layer was washed twice with water (150ml). The organic layer was separated and concentrated to get the titled compound.

Yield: 70%

Purity: 95% (by HPLC)

Example 22B: Preparation of 3-(difluoromethyl)-1-methyl-1H-pyrazole

Triethyl amine (50g) was added to a mixture of 3-(difluoromethyl)-1-methyl-1H-pyrazole-4-carboxylic acid (170g), copper powder (10.8g), copper oxide (9.67g) in sulfolane (252g) at a temperature of about 20 to 50° C. The reaction mixture was stirred at a temperature of 150° C. During decarboxylation carbon dioxide gas was released and the product mixture was collected in another vessel. The collected product mixture consisted of two layers i.e., lower layer and upper layer. The layers were separated and upper layer which consisted of TBA was recycled back to reactor. Dichloromethane (150 ml) was added to the lower layer. The organic layer was washed twice with an aqueous solution of hydrochloric acid solution (1N, 150ml). The layers were separated and the organic layer was washed twice with water (150ml). The organic layer was separated and concentrated to get the titled compound.

Yield: 70%
Purity: 95% (by HPLC)

Example 22C: Preparation of 3-(difluoromethyl)-1-methyl-1H-pyrazole

Diisopropylethyl amine (75g) was added to a mixture of 3-(difluoromethyl)-1-methyl-1H-pyrazole-4-carboxylic acid (170g), Copper powder (10.8g), copper oxide (9.67g) in sulfolane (252g) at a temperature of about 20 to 50° C. The reaction mixture was stirred at a temperature of 150° C. During decarboxylation carbon dioxide gas was released and the product mixture was collected in another vessel. The collected product mixture consisted of two layers i.e., lower layer and upper layer. The layers were separated and upper layer which consisted of TBA was recycled back to reactor. Dichloromethane (150ml) was added to the lower layer. The organic layer was washed twice with an aqueous solution of hydrochloric acid solution (1N, 150ml). The layers were separated and the organic layer was washed twice with water (150ml). The organic layer was separated and concentrated to get the titled compound.

Yield: 70%
Purity: 95% (by HPLC)

Example 22D: Preparation of 3-(difluoromethyl)-1-methyl-1H-pyrazole

Diisopropyl amine (50g) was added to a mixture of 3-(difluoromethyl)-1-methyl-1H-pyrazole-4-carboxylic acid (170g), copper powder (10.8g), Copper oxide (9.67g) in sulfolane (252g) at a temperature of about 20 to 50° C. The reaction mixture was stirred at a temperature of 150° C. During decarboxylation carbon dioxide gas was released and the product mixture was collected in another vessel. The collected product mixture consisted of two layers i.e., lower layer and upper layer. The layers were separated and upper layer which consisted of TBA was recycled back to reactor. Dichloromethane (150ml) was added to the lower layer. The organic layer was washed twice with an aqueous solution of hydrochloric acid solution (IN, 150ml). The layers were separated and the organic layer was washed twice with water (150ml). The organic layer was separated and concentrated to get the titled compound.

Yield: 70%
Purity: 95% (by HPLC)

We claim:

1. A process for preparation of a compound of formula II,

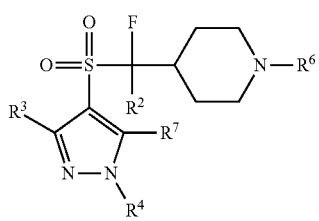

Formula II wherein $R^2$ is F, $C_1$-$C_4$ alkyl, or $C_1$-$C_4$ haloalkyl, $R^3$ is, F, $C_1$-$C_4$ alkyl, or $C_1$-$C_4$ haloalkyl, $R^4$ is $C_1$-$C_4$ alkyl, $R^6$ is H or a protecting group or a salt thereof, and $R^7$ is H, Cl or trialkylsilyl, comprising the steps of:

a) reacting a compound of formula VII with elemental sulfur in the presence of a base, a catalyst and a reducing agent to give a compound of formula VI;

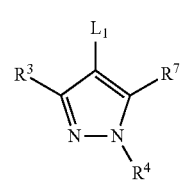

Formula VII

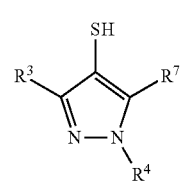

Formula VI wherein $R^3$, $R^4$ and $R^7$ are as defined above and $L_1$ is a leaving group;

b) reacting the compound of formula VI with a compound of formula VIII, to give a compound of formula V;

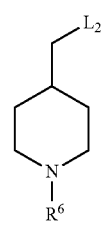

Formula VIII

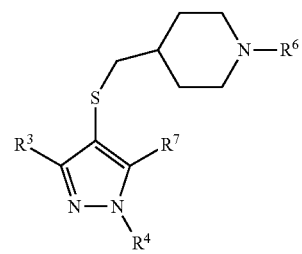

Formula V wherein $L_2$ is a leaving group and $R^3$, $R^4$, $R^6$ and $R^7$ are as defined above; and c) converting the compound of formula V to the compound of formula II.

2. A process for preparation of a compound of formula II

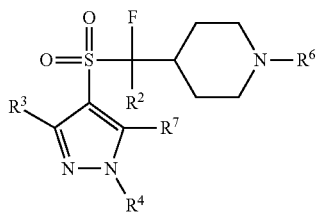
Formula II wherein $R^2$ is F, $C_1$-$C_4$ alkyl, or $C_1$-$C_4$ haloalkyl,
$R^3$ is H, F, $C_1$-$C_4$ alkyl, or $C_1$-$C_4$ haloalkyl,
$R^4$ is $C_1$-$C_4$ alkyl,
$R^6$ is H or a protecting group or a salt thereof, and
$R^7$ is H, Cl or trialkylsilyl;
comprising the steps of:
a) reacting a compound of formula VII with elemental sulfur in the presence of base and a catalyst to give a compound of formula VIB,

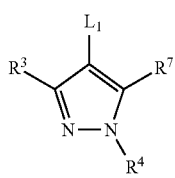
Formula VII

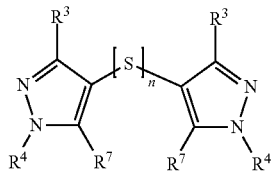
Formula VIB wherein $R^3$, $R^4$, and $R^7$ are as defined above, $L_1$ is a leaving group, and n is 2-8;
b) reacting the compound of formula VIB with a compound of formula VIII, to give a compound of formula V;

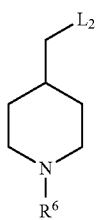
Formula VIII

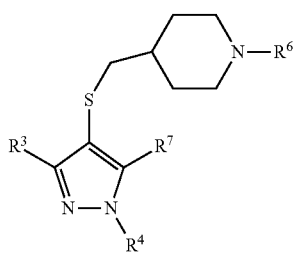
Formula V wherein $R^6$ is as defined above and L2 is a leaving group, and
c) converting the compound of formula V to the compound of formula II.

3. The process of claim 1,
wherein step c) further comprises:
fluorinating the compound of formula V to give a compound of formula IV;

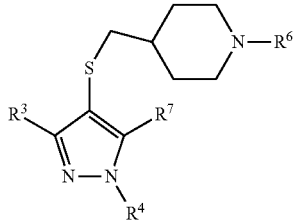
Formula V

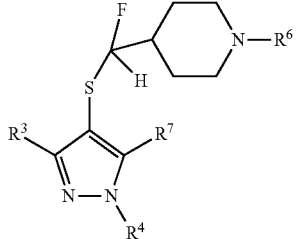
Formula IV oxidizing the compound of formula IV to give a compound of formula III; and

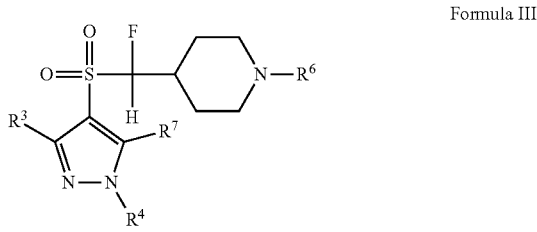
Formula III converting the compound of formula III to the compound of formula II.

4. The process of claim 3, wherein the steps of fluorination and oxidization are carried out without isolating the compound of formula IV.

5. A process for preparation of a compound of formula IV

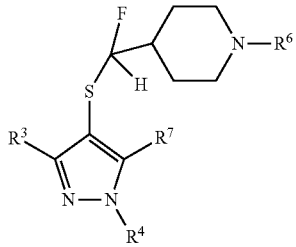
Formula IV wherein $R^3$ is H, F, $C_1$-$C_4$ alkyl, or $C_1$-$C_4$ haloalkyl,
$R^4$ is $C_1$-$C_4$ alkyl,
$R^6$ is H or a protecting group or a salt thereof; and
$R^7$ is H, Cl or trialkylsilyl;
comprising fluorinating a compound of formula V,

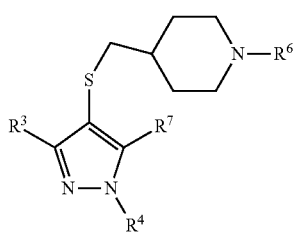

Formula V wherein $R^3$, $R^4$, $R^6$ and $R^7$ are as defined above, to obtain a compound of formula IV.

6. A process for preparation of a compound of formula III

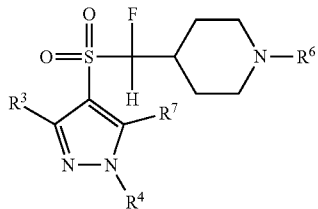

Formula III wherein $R^3$ is H, F, $C_1$-$C_4$ alkyl, or $C_1$-$C_4$ haloalkyl,
$R^4$ is $C_1$-$C_4$ alkyl,
$R^6$ is H or a protecting group or a salt thereof, and
$R^7$ is H, Cl or trialkylsilyl;
comprising oxidizing a compound of formula IV

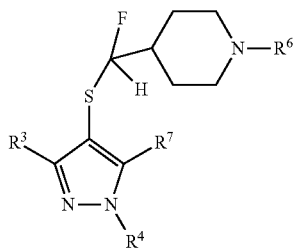

Formula IV wherein $R^3$, $R^4$, $R^6$ and $R^7$ are as defined above, to obtain a compound of formula III.

7. A compound of formula VIB,

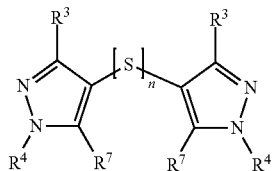

Formula VIB wherein $R^3$ is F, $C_1$-$C_4$ alkyl, or $C_1$-$C_4$ haloalkyl,
$R^4$ is $C_1$-$C_4$ alkyl,
$R^7$ is H, Cl or trialkylsilyl, and
n is 2-8.

8. A compound of formula IV,

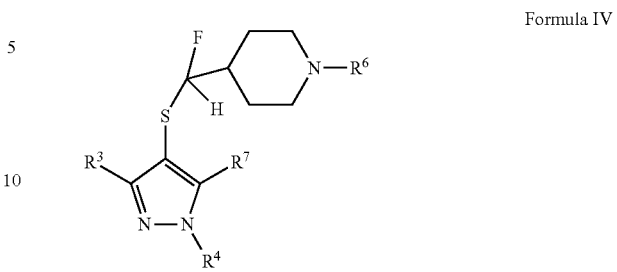

Formula IV wherein $R^3$ is H, F, $C_1$-$C_4$ alkyl, or $C_1$-$C_4$ haloalkyl,
$R^4$ is Ci-C4 alkyl,
$^6$ is H or a protecting group or a salt thereof, and
$R^7$ is H, Cl or trialkylsilyl.

9. The process of claim 1, wherein the base is selected from the group consisting of potassium carbonate, sodium carbonate, cesium carbonate, potassium bicarbonate, sodium bicarbonate and cesium bicarbonate.

10. The process of claim 1, wherein the catalyst is selected from the group consisting of copper powder, copper chloride, copper bromide, and copper iodide.

11. The process of claim 1, wherein reducing agent is selected from the group consisting of zinc/acetic acid, zinc/alcoholic potassium hydroxide, sodium borohydride, potassium borohydride, lithium aluminum hydride, triphenylphosphine/HC1, tris(2-carboxyethyl)phosphine, and borane.

12. The process of claim 4, wherein the step of fluorination is carried out in the presence of a fluorinating agent selected from the group consisting of 1-fluoropyridinium triflate, 1-fluoropyridinium tetrafluoroborate, 1-fluoro-2,4,6-trimethylpyridinium tetrafluoroborate, 1-fluoro-2,4,6-trimethylpyridinium triflate, 1-fluoro-2, 6-dichloropyridinium triflate, 2,6- dichloro- 1-fluoropyridinium tetrafluoroborate, 1- fluoro-4-methylpyridinium triflate, and 1-fluoro-4-methylpyridinium tetrafluoroborate.

13. The process of claim 4, wherein the step of oxidation is carried out in the presence of an oxidizing agent selected from the group consisting of hydrogen peroxide/sodium tungstate, peracetic acid, benzyl hydroperoxide, ethylbenzene hydroperoxide, cumyl hydroperoxide, sodium hypochlorite, oxalic acid dihydrate/hydrogen peroxide, meta-chloroperoxybenzoic acid, urea-hydrogen peroxide adduct, Permanganate/manganese dioxide, Ruthenium chloride hydrate/sodium periodate and oxone.

14. The process of claim 3, wherein converting the compound of formula III to a compound of formula II is carried out using alkylating agent selected from the group consisting of bromoalkane, chloroalkane, iodoalkane, diazoalkane, dialkylcarbonate, dialkylsulfonate in the presence of a base selected from sodium hydride, potassium hydride, sodium ethoxide, sodium methoxide, lithium tert-butoxide, sodium tert-butoxide, potassium tert-butoxide, triethylamine, n-butylamine, t-butylamine, pyridine, methyl lithium, n-butyl lithium, lithium diisopropyl amide, lithium 2,2,6,6-tetramethylpiperidine, sodium bis(trimethylsilyl)amide, lithium bis(trimethylsilyl)amide, potassium bis(trimethylsilyl)amide, and lithium diethylamide.

15. The process of claim 2, wherein the base is selected from the group consisting of potassium carbonate, sodium carbonate, cesium carbonate, potassium bicarbonate, sodium bicarbonate and cesium bicarbonate.

16. The process of claim 2, wherein the catalyst is selected from the group consisting of copper powder, copper chloride, copper bromide, and copper iodide.

17. The process of claim 5, wherein the step of fluorination is carried out in the presence of a fluorinating agent selected from the group consisting of 1-fluoropyridinium triflate, 1-fluoropyridinium tetrafluoroborate, 1-fluoro-2,4,6-trimethylpyridinium tetrafluoroborate, 1-fluoro-2,4,6-trimethylpyridinium triflate, 1-fluoro-2, 6- dichloropyridinium triflate, 2,6- dichloro- 1-fluoropyridinium tetrafluoroborate, 1-fluoro-4- methylpyridinium triflate, and 1-fluoro-4-methylpyridinium tetrafluoroborate.

18. The process of claim 6, wherein the step of oxidation is carried out in the presence of an oxidizing agent selected from the group consisting of hydrogen peroxide/sodium tungstate, peracetic acid, benzyl hydroperoxide, ethylbenzene hydroperoxide, cumyl hydroperoxide, sodium hypochlorite, oxalic acid dihydrate/hydrogen peroxide, meta-chloroperoxybenzoic acid, urea-hydrogen peroxide adduct, Permanganate/manganese dioxide, Ruthenium chloride hydrate/sodium periodate and oxone.

19. The process of claim 2, wherein step c) further comprises:
fluorinating the compound of formula V to give a compound of formula IV;

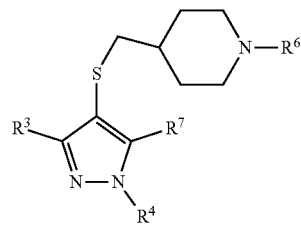

Formula V

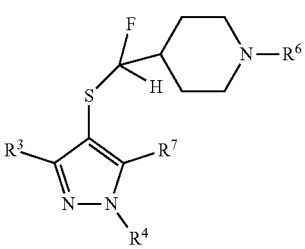

Formula IV oxidizing the compound of formula IV to give a compound of formula III; and

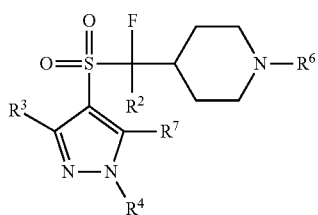

Formula II converting the compound of formula III to the compound of formula II.

20. The process of claim 19, wherein converting the compound of formula III to a compound of formula II is carried out using alkylating agent selected from the group consisting of bromoalkane, chloroalkane, iodoalkane, diazoalkane, dialkylcarbonate, dialkylsulfonate in the presence of a base selected from sodium hydride, potassium hydride, sodium ethoxide, sodium methoxide, lithium tert-butoxide, sodium tert-butoxide, potassium tert-butoxide, triethylamine, n-butylamine, t-butylamine, pyridine, methyl lithium, n-butyl lithium, lithium diisopropylamide, lithium 2,2,6,6-tetramethylpiperidine, sodium bi s(trimethylsilyl)amide, lithium bis(trimethylsilyl)amide, potassium bis(trimethylsilyl)amide, and lithium diethylamide.

21. The compound of claim 20, wherein $R^3$ is difluoromethyl.

22. The compound of claim 20, wherein $R^4$ is methyl.

23. The compound of claim 20, wherein $R^7$ is H or Cl.

24. The compound of claim 20, wherein the compound is of formula IVA:

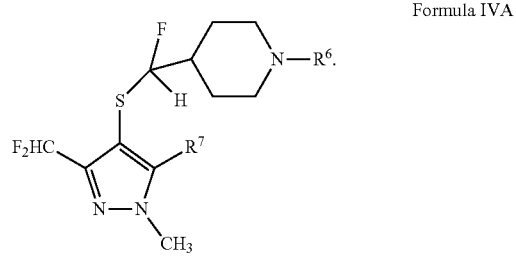

Formula IVA

25. The compound of claim 24, wherein the compound is tert-butyl-4-[{[3-(difluoromethyl)-1-methyl-1H-pyrazol-4-yl]sulfanyl}(fluoro)methyl]piperidine-1-carboxylate.

26. A process for preparation of a compound of formula Z,

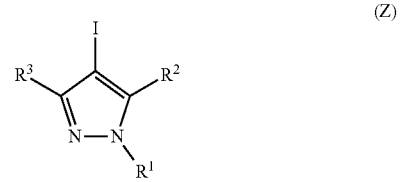

(Z)

wherein $R^1$ is hydrogen, $C_1$-$C_6$ alkyl optionally substituted with one or more halogen atoms, $C_3$-$C_6$ cycloalkyl, or arylalkyl;
$R^2$ is hydrogen, $C_1$-$C_6$ alkyl, $C_3$-$C_6$ cycloalkyl, arylalkyl, or aryl;
$R^3$ is $C_1$-$C_6$ alkyl substituted with one or more halogen atoms;
wherein each halogen atom is independently selected from fluorine, chlorine, bromine, and iodine;
comprising the steps of:
a) decarboxylating a compound of formula X to obtain a compound of formula Y; and

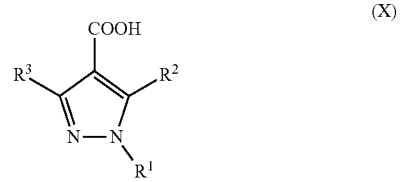

(X)

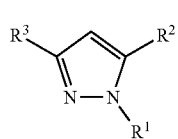

(Y)

b) iodinating the compound of formula Y to obtain the compound of formula Z.

27. The process of claim 26, wherein step a) comprises decarboxylating the compound of formula X using a copper reagent in the presence of an aliphatic amine.

28. The process of claim 27, wherein the copper reagent is selected from the group consisting of copper powder, cuprous oxide, cupric oxide, copper chloride, and copper iodide, or any combination thereof.

29. The process of claim 27, wherein the aliphatic amine is straight chain or branched chain alkyl amine selected from the group consisting of methylamine, ethylamine, triethylamine, diethylmethylamine, isopropylamine, diisopropylamine, diisopropylmethylamine, diisopropylethylamine, n-butylamine, tertiary butylamine, and tributylamine, or any combination thereof.

30. The process of claim 26, wherein the step of iodination is carried out using iodine and potassium iodate in the presence of an organic acid.

31. The process of claim 30, wherein the organic acid is a lower alkyl sulfonic acid, an aryl sulfonic acid, or a carboxylic acid selected from the group consisting of acetic acid, oxalic acid, pyruvic acid, benzoic acid, methanesulfonic acid, benzenesulfonic acid, and p-toluenesulfonic acid, or any combination thereof.

32. The process of claim 26, wherein the compound of formula Z is 3-(difluoromethyl)-4-iodo-1-methyl-1H-pyrazole.

* * * * *